United States Patent
Han et al.

(10) Patent No.: US 7,144,505 B2
(45) Date of Patent: Dec. 5, 2006

(54) MELT-SPUN POLYSULFONE SEMIPERMEABLE MEMBRANES AND METHODS FOR MAKING THE SAME

(75) Inventors: Wenli Han, Weston, FL (US); Martin Ketterer, Apex, NC (US); Jonnie Lee, Pembroke Pines, FL (US); Thanh Nguyen, Pembroke Pines, FL (US); George Washington, Miramar, FL (US); Delores Jordan, Miami, FL (US); Dibyendu De, Pembroke Pines, FL (US)

(73) Assignees: Baxter International Inc., Deerfield, IL (US); Baxter Healthare S.A., Zurich (CH)

( * ) Notice: Subject to any disclaimer, the term of this patent is extended or adjusted under 35 U.S.C. 154(b) by 0 days.

(21) Appl. No.: 10/327,564

(22) Filed: Dec. 20, 2002

(65) Prior Publication Data

US 2004/0026315 A1 Feb. 12, 2004

Related U.S. Application Data

(60) Continuation-in-part of application No. 09/767,558, filed on Jan. 22, 2001, now Pat. No. 6,881,337, which is a continuation of application No. 09/317,657, filed on May 24, 1999, now Pat. No. 6,218,441, which is a division of application No. 08/932,680, filed on Sep. 18, 1997, now abandoned.

(51) Int. Cl.
*B01D 39/00* (2006.01)
*B01D 39/14* (2006.01)
*B01D 33/21* (2006.01)

(52) U.S. Cl. .................. 210/500.41; 210/500.22; 210/500.42; 210/500.27; 210/500.23; 264/41; 264/48; 264/49

(58) Field of Classification Search .......... 210/500.41, 210/500.27, 500.31, 500.42, 500.22, 500.23; 264/41, 79, 80
See application file for complete search history.

(56) References Cited

U.S. PATENT DOCUMENTS 3,763,055 A 10/1973 White et al.
(Continued)

FOREIGN PATENT DOCUMENTS

EP 0121911 A2 6/1984
(Continued)

OTHER PUBLICATIONS

Cabasso et al., "Polysulfone Hollow Fibers. I. Spinning and Properties," J. Appl. Polymer Sci. 20:2377-2394 (1976).
(Continued)

*Primary Examiner*—Ana Fortuna
(74) *Attorney, Agent, or Firm*—Gina M. Bicknell; Ted J. Barthel

(57) ABSTRACT

The present invention provides, inter alia, a composition useful for producing a homogeneous, semipermeable membrane, the composition comprising a polysulfone semipermeable membrane, the polysulfone semipermeable membrane comprising a mixture of: an ultra-high-molecular-weight hydrophilic polymer, a polysulfone compound and a solvent for the polysulfone compound, and the polysulfone semipermeable membrane having a homogeneous structure such that the polysulfone semipermeable membrane has a substantially uniform structure. Another aspect of this invention discloses methods for fabricating semipermeable membranes by homogeneously mixing the composition, melting the composition, and melt-spinning the molten composition. Another aspect of the present invention includes homogeneous, melt-spun, semipermeable membranes useful for liquid separation processes, such as, but not limited to, microfiltration, ultrafiltration, dialysis, and reverse osmosis.

18 Claims, 5 Drawing Sheets

U.S. PATENT DOCUMENTS

| | | | |
|---|---|---|---|
| 3,993,560 A | 11/1976 | Halpern | |
| 4,276,173 A | 6/1981 | Kell et al. | |
| 4,474,690 A | 10/1984 | Nylen | |
| 4,612,119 A | 9/1986 | Eguchi | |
| 4,720,343 A | 1/1988 | Walch et al. | |
| 4,780,205 A | 10/1988 | Murakami et al. | |
| 4,798,847 A | 1/1989 | Roesink et al. | |
| 4,818,387 A | 4/1989 | Ikeda et al. | |
| 4,834,882 A | 5/1989 | Kataoka et al. | |
| 4,874,522 A | 10/1989 | Okamoto et al. | |
| 4,900,449 A | 2/1990 | Kraus et al. | |
| 4,906,375 A * | 3/1990 | Heilmann | 210/500.23 |
| 4,925,534 A | 5/1990 | Kataoka et al. | |
| 4,964,990 A | 10/1990 | Kraus et al. | |
| 4,968,733 A | 11/1990 | Muller et al. | |
| 4,970,034 A | 11/1990 | Ly et al. | |
| 4,980,063 A | 12/1990 | Mahoney et al. | |
| 5,049,169 A | 9/1991 | Teramoto et al. | |
| 5,055,631 A | 10/1991 | Sartori et al. | |
| 5,062,866 A | 11/1991 | Ho | |
| 5,071,448 A | 12/1991 | Bikson et al. | |
| 5,076,925 A | 12/1991 | Roesink et al. | |
| 5,096,968 A | 3/1992 | Sasaki et al. | |
| 5,102,917 A | 4/1992 | Bedwell et al. | |
| 5,131,928 A | 7/1992 | Blackman et al. | |
| 5,151,222 A | 9/1992 | Ruffoni | |
| 5,151,227 A * | 9/1992 | Nguyen et al. | 264/41 |
| 5,187,010 A | 2/1993 | Parham et al. | |
| 5,232,601 A | 8/1993 | Chu et al. | |
| 5,236,644 A | 8/1993 | Parham et al. | |
| 5,246,582 A | 9/1993 | Sluma et al. | |
| 5,259,950 A | 11/1993 | Shiro et al. | |
| 5,279,739 A | 1/1994 | Pemawansa | |
| 5,340,480 A * | 8/1994 | Kawata et al. | 210/500.23 |
| 5,376,274 A * | 12/1994 | Muller et al. | 210/500.41 |
| 5,385,670 A | 1/1995 | McDonogh et al. | |
| 5,418,061 A | 5/1995 | Parham et al. | |
| 5,436,068 A | 7/1995 | Kobayashi et al. | |
| 5,462,867 A | 10/1995 | Azad et al. | |
| 5,503,746 A | 4/1996 | Gagnon | |
| 5,643,452 A | 7/1997 | Althin et al. | |
| 5,698,101 A | 12/1997 | Kopp et al. | |
| 5,738,791 A * | 4/1998 | Schomaker et al. | 210/638 |
| 5,906,742 A | 5/1999 | Wang et al. | |
| 5,938,929 A | 8/1999 | Shimagaki et al. | |
| 5,983,916 A * | 11/1999 | Daul et al. | 137/15.01 |
| 6,026,968 A | 2/2000 | Hachisuka et al. | |
| 6,103,117 A * | 8/2000 | Shimagaki et al. | 210/321.71 |
| 6,146,747 A * | 11/2000 | Wang et al. | 428/310.5 |
| 6,218,441 B1 * | 4/2001 | Meluch et al. | 264/129 |
| 6,284,137 B1 * | 9/2001 | Hajikano et al. | 210/500.41 |
| 6,881,337 B1 * | 4/2005 | Meluch et al. | 210/500.41 |

FOREIGN PATENT DOCUMENTS

| | | |
|---|---|---|
| EP | 249932 | 12/1987 |
| EP | 0568045 A1 | 4/1993 |
| EP | 598 690 A2 | 5/1994 |
| JP | 57-094310 | 11/1982 |
| JP | 61-90672 | 8/1986 |
| JP | 5-148383 | 6/1993 |
| JP | 5-262910 | 10/1993 |
| WO | 90/05018 | 10/1989 |

OTHER PUBLICATIONS

Cabasson et al., "Polysulfone Hollow fibers. II. Morphology," J. Appl. Polymer Sci. 21: 165-180 (1977).

Hu et al., "Preparation of Polysulfone (PSF) Thermal Phase Inversion Membrane," Chem. Abstracts, vol. 123, No. 6, Aug. 7, 1995.

ASTM Designation: D 1238-99, Standard Test method for Melt Flow Rates of Thermoplastics by Extrusion Plastometer, pp. 1-10, Apr. 2000.

* cited by examiner

METHOD I

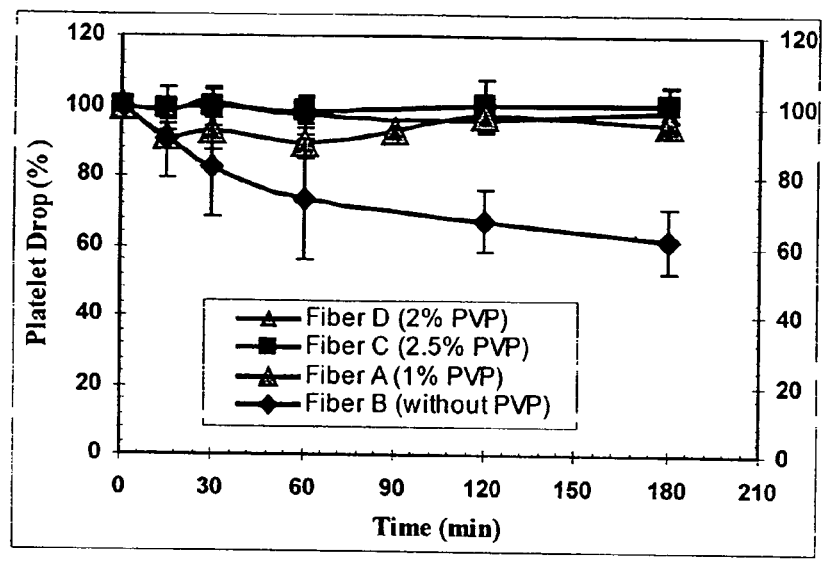
FIG 9
Figure 6: Cross section
Figure 7: Fiber wall
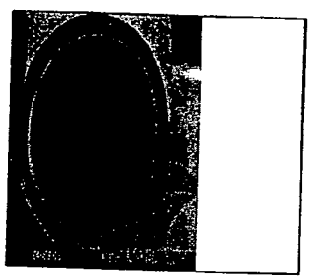
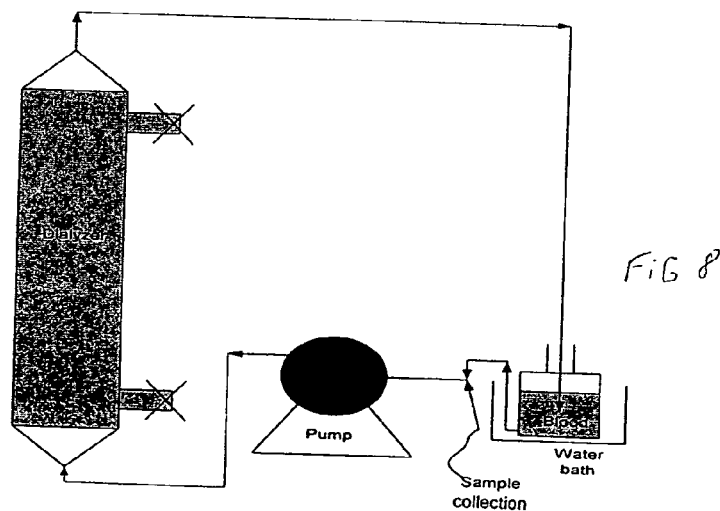
FIG 8

MELT-SPUN POLYSULFONE SEMIPERMEABLE MEMBRANES AND METHODS FOR MAKING THE SAME

RELATED APPLICATIONS

This is a continuation-in-part of U.S. patent application Ser. No. 09/767,558, filed on Jan. 22, 2001 now U.S. Pat. No. 6,881,337 which is a continuation of U.S. patent application Ser. No. 09/317,657, filed on May 24, 1999, now issued as U.S. Pat. No. 6,218,441, which is a divisional of U.S. patent application Ser. No. 08/932,680, filed on Sep. 18, 1997, now abandoned, the disclosures of which are incorporated herein by reference.

BACKGROUND OF THE INVENTION

The present invention concerns polysulfone semipermeable membranes and methods for making the same.

Contemporary semipermeable membranes are available in a variety of forms such as sheets, tubes, and hollow fibers. A "hollow fiber" is generally a hollow cylindrical structure in which the wall functions as a permeable, non-permeable, or semipermeable (i.e., selectively permeable) membrane depending upon the application. Generally, hollow fibers are used as cylindrical membranes that permit selective exchange of materials across the walls.

Liquid-separation processes utilizing membranes having selective permeabilities, such processes including ultrafiltration, microfiltration, dialysis, reverse osmosis, or the like, require a variety of materials adapted for diversified applications. For example, semipermeable membranes are currently favored for use in extracorporeal blood treatments including hemodialysis, hemofiltration, and hemodiafiltration. In such cases, the membranes typically comprise hollow fibers bundled together and assembled in a casing in a manner allowing blood to flow simultaneously in a parallel manner through the lumina of the fibers while a blood-cleansing liquid is simultaneously passed through the casing so as to bathe the exterior surfaces of the hollow fibers with the liquid.

Compounds utilized for selectively permeable membranes have included polymers, such as cellulose, cellulose acetate, polyamide, polyacrylonitrile, polyvinylalcohol, polymethyl methacrylate, polysulfone, polyolefin, or the like, depending upon the use of the membranes. Polysulfone compounds are of particular interest as they have, inter alia, excellent physical and chemical properties, such as resistance to heat, resistance to acids, resistance to alkali, and resistance to oxidation. Polysulfone compounds have been found to be biocompatible, capable of forming excellent pores and interstitia, and chemically inert to such compounds as bleach, disinfectants, and salt solutions. Polysulfone compounds can be sterilized by a number of methods, such as ethylene oxide (EtO), gamma irradiation, steam autoclave, and heated citric acid. Additionally, polysulfone compounds possess sufficient strength and resistance to wear to withstand repeated use and sterilization cycles.

Conventionally, polysulfone hollow fibers have been formed by solution-spinning techniques. Producing polysulfone hollow fibers by solution-spinning techniques typically involves dissolving a polysulfone compound in a relatively large amount of an aprotic solvent and a non-solvent, then extruding the solution through a spinneret. For solution spinning, a "solvent" is a compound in which the polysulfone compound substantially dissolves at the membrane-fabrication temperature (i.e., ambient temperature). For solution spinning, a "non-solvent" is a compound in which the polysulfone compound is substantially insoluble at the membrane-fabrication temperature. For solution-spinning techniques, the solvents must be sufficient to substantially dissolve the polysulfone compound and produce a homogeneous liquid at ambient temperature (membrane fabrication temperature).

The solvents and non-solvents utilized for solution-spinning techniques require that the membranes be extensively leached and rinsed after fabrication, as even residual amounts left in the membranes can cause unacceptable contamination of fluids treated using the membranes. Avoiding such contamination is particularly important in membranes used for the treatment of blood by dialysis or the desalination of water by reverse osmosis. When fabricating hollow-fiber membranes utilizing solution spinning techniques, removal of the core liquid used to form the fiber lumen is especially difficult. Following removal of the solvents, non-solvents, and core liquid, a non-volatile, water-soluble compound must then be added to preserve the membrane pore structure prior to drying the membrane. The non-volatile material also serves as a surfactant for later rewetting of the membranes. Such a process is known as "replasticization."

Solution-spinning techniques require the inclusion of large amounts of solvents and non-solvents many of which are generally toxic and can be difficult to extract from the resulting polysulfone fiber. Moreover, the significant amount and high level of toxicity of certain solvents and non-solvents removed from the fibers may create a hazardous waste-disposal problem.

Moreover, conventional solution-spinning techniques produce asymmetric polysulfone membranes (i.e., non-homogeneous membrane porosity progressing through the thickness dimension of the membrane). That is, a non-homogeneous membrane has a dense skin or micro-porous barrier layer on one (or both) of the major surfaces of the membrane. The dense skin or micro-porous barrier layer comprises a relatively small portion of the membrane but contributes a disproportionally large amount of control on the permeability characteristics of the membrane.

Accordingly, there is a need for a polysulfone composition and simple method for the production of polysulfone semipermeable membranes which composition and method minimizes toxic waste by-products. Additionally, there is a need for a method for the production of polysulfone semipermeable membranes wherein the solvents, non-solvents, and processing aids used in the manufacture of the membranes are easily removed from the membranes after fabrication and/or are of relatively low toxicity. There is also a need for polysulfone semipermeable membranes having a more uniform structure throughout the thickness dimension (i.e., a homogeneous polysulfone membrane) so that the entire thickness dimension controls the permeability of the membrane.

SUMMARY OF THE INVENTION

In general, the present invention provides, inter alia, a novel method and polysulfone composition for preparing a homogeneous, semipermeable polysulfone membrane by melt-spinning. The polysulfone composition comprises a liquid mixture of an ultra-high-molecular-weight (UHMW) hydrophilic polymer such as polyvinylpyrrolidone, a polysulfone compound, a solvent, and a non-solvent that are relatively non-toxic and that preferably do not deleteriously affect the environment.

The solvent may be selected from the group consisting of tetramethylene sulfone ("sulfolane"); 3-methyl sulfolane; benzophenone; n,n-dimethylacetamide; 2-pyrrolidone; 3-methylsulfolene; pyridine; thiopene; o-dichlorobenzene; 1-chloronaphthalene; methyl salicylate; anisole; o-nitroanisole; diphenyl ether; diphenoxy methane; acetophenone; p-methoxyphenyl-2-ethanol; 2-piperidine; antipyrine; diethyl phthalate; diphenyl sulfone; diphenyl sulfoxide; phthalic acid, dioctyl ester; phthalic acid, dimethyl ester; phthalic acid, diethyl ester; phthalic acid, dibutyl ester; phthalic acid, bis(2-ethylhexyl) ester; phthalic acid, benzyl butyl ester; and phenyl sulfide.

Especially good results have been achieved when the solvent comprises sulfolane.

The non-solvent may be selected from the group consisting of poly(ethylene glycol), di(ethylene glycol), tri(ethylene glycol), glycerol, 1,1-diethylurea; 1,3-diethylurea; dinitrotoluene; 1,2-ethane diamine; diphenylamine; toluenediamine; o-toluic acid; m-toluic acid; toluene-3,4-diamine; dibutyl phthalate; piperidine; decalin; cyclohexane; cyclohexene; chlorocyclohexane; "cellosolve" solvent; n,n-dimethylbenzylamine; paraffin; mineral oil; mineral wax; tallow amine; triethanol amine; lauryl methacrylate; stearic acid; ethylene glycol; tetra(ethylene glycol); diethyl adipate; d-sorbitol; chlorotriphenyl stannane; resorcinol; 2-methyl-8-quinolinol; quinaldine; 4-phenylpyridine; phosphorothioic acid, o,o-diethyl o-(p-nitrophenyl) ester; N,N-dimethyl-p-phenylene diamine; 2,6-dimethoxyphenol; 4-allyl-2-methoxyphenol; phenanthridine; 2-naphthylamine; 1-naphthylamine; 1-naphthol; 2-naphthalenethiol; 1-bomonaphthalene; levulinic acid; phenyl pyrrol-2-yl ketone; phenyl 4-pyridyl ketone; isothiocyanic acid, m-nitrophenyl ester; 2-methyl-1H-indole; 4-methyl imidazole; imidazole; 1,7-heptanediol; 9H-fluoren-9-one; ferrocene; 2,2',2"-nitrilotriethanol; 2,2'-iminodiethanol; dibenzofuran; cyclohexaneacetic acid; cyanamide; courmarin; 2,2'-bipyridine; benzoic acid; benzenepropionic acid; o-dinitrobenzene; 9-methyl-9-azabicyclo(3.3.1)nonan-3-one; chlorodiphenylarsine; antimony bromide; p-anisidine; o-anisaldehyde; adiponitrile; p-amino acetophenone; monoacetin; diacetin; triacetin; pentoxane; 4-benzoylbiphenyl; methyl oleate; triethylphosphate; butyrolactone; terphenyl; tetradecanol; polychlorinated biphenyl ("Aroclor 1242"); myristic acid; methacrylic acid, dodecyl ester; isocyanic acid; methylenedi-p-phenylene ester; 2-((2-hexyloxy)ethoxy) ethanol; 4-nitro biphenyl; benzyl ether; benzenesulfonyl chloride; 2,4-diisocyanato-1-1-methyl benzene; adipic acid, diethyl ester; 2'-nitro-acetophenone; 1'-acetonaphthone; tetradecanone; (dichlorophenyl)trichlorosilane; dichlorodiphenyl silane; phosphorothioic acid, o,o-diethyl o-(p-nitrophenyl) ester; phosphoric acid, tri-o-tolyl ester; phosphoric acid, triphenyl ester; phosphoric acid, tributyl ester; phenyl phosphorous dichloride; p-nitrophenol; isocyanic acid, methyl-m-phenylene ester; 2,2'-iminodiethanol; N-(2-aminoethyl)-N'-(2-((2-aminoethyl)amino)ethyl) 1,2-ethanediamine; 2,6-di-tert-butyl p-cresol; chloro biphenyl; 4-biphenylamine; benzyl ether; benzenesulfonyl chloride; 1,2-(methylenedioxy)-4-propenyl benzene; 2,4-diisocyanato-1-methyl benzene; chlorodinitro benzene (mixed isomers); hexahydro 2H-azepin-2-one; 4,4'-methylenedianiline; 1'-acetonaphthone; mercapto acetic acid; and acetanilide. Especially good results have been achieved when the non-solvent comprises poly(ethylene glycol), di(ethylene glycol), tri(ethylene glycol), or a mixture thereof.

The solvent and non-solvent are present in a ratio useful to form a semipermeable, polysulfone membrane useful for performing liquid-separation processes.

According to another aspect of the invention, a "melt-spinning" or "melt-extrusion" method is provided for producing semipermeable, polysulfone membranes. The melt-spinning method includes the steps of: (1) forming a composition comprising a UHMW hydrophilic polymer, preferably, polyvinylpyrrolidone, a polysulfone compound, a solvent selected from the foregoing group of candidate solvents, and, a non-solvent selected from the foregoing group of candidate non-solvents; (2) heating the composition to a temperature at which the composition becomes a homogeneous liquid (i.e., a temperature greater than ambient); (3) extruding the composition through an extrusion die (such as a single or multi-holed hollow-fiber die (termed a "spinneret"); and (4) passing the extrudate through a quench zone in which the extrudate gels and solidifies, thereby forming the membrane.

According to another aspect of the present invention, melt-spun, semipermeable, polysulfone membranes are provided having a uniform structure throughout the thickness dimension of the membrane (i.e., a "homogeneous" membrane structure) useful for liquid separations, such as, but not limited to, microfiltration, ultrafiltration, reverse osmosis, and dialysis.

BRIEF DESCRIPTION OF THE DRAWINGS

FIG. 6 illustrates a scanning electron microscope photograph of a cross-section of a representative polysulfone hollow-fiber membrane including ultra-high-molecular-weight hydrophillic polymer.

FIG. 7 illustrates a scanning electron microscope photograph of a cross-section of a portion of a fiber wall of the representative polysulfone hollow-fiber membrane of FIG. 6 including ultra-high-molecular-weight hydrophillic polymer.

FIG. 8 illustrates schematically an in-vitro platelet test system discussed in Example No. 8.

FIG. 9 illustrates in-vitro anti-thrombogenic evaluation using bovine blood of Example No. 9.

DETAILED DESCRIPTION

Figure 1:
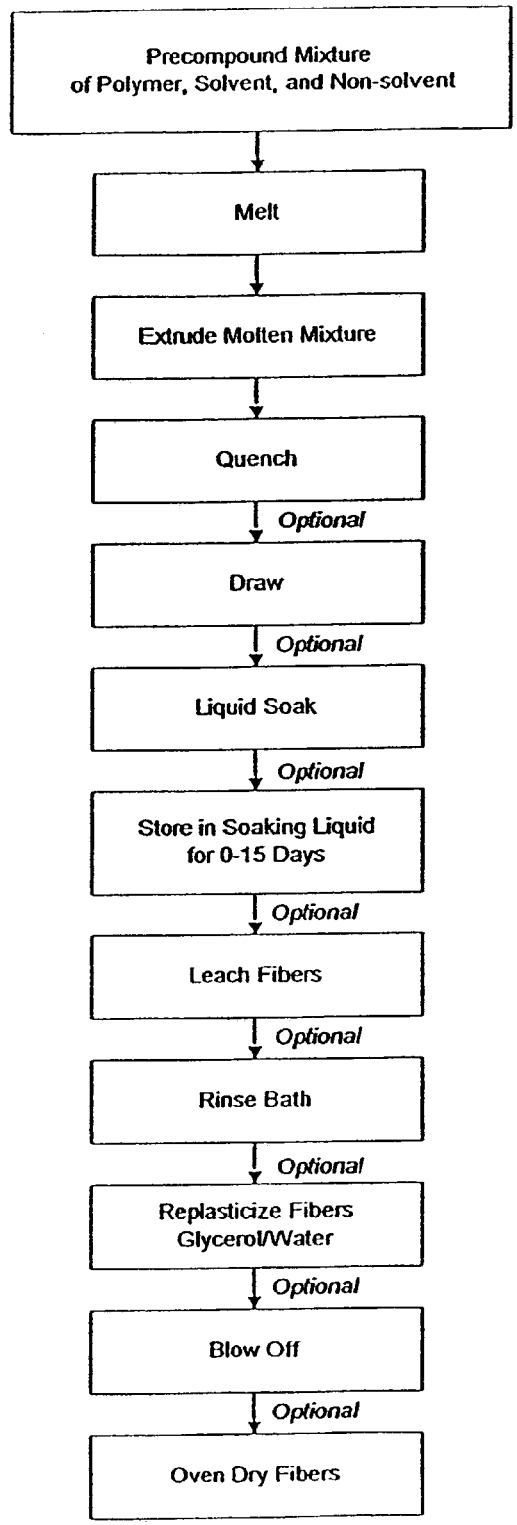
FIG. 1 illustrates a preferred embodiment of the process for fabricating homogeneous polysulfone hollow fibers (as a representative membrane configuration).

This invention encompasses, inter alia, compositions useful for forming, by melt-spinning, polysulfone semipermeable membranes. The compositions comprise a ultra-high-molecular-weight hydrophillic polymer, preferably polyvinylpyrrolidone (Kollidon 90F, MW=1,000,000–1,500,000 daltons), a polysulfone compound, a solvent and, a non-solvent. In the composition, the solvent and non-solvent are present in a ratio useful to form a semipermeable membrane useful for performing liquid separation processes. Membranes that are melt-spun using such compositions are homogeneous. That is, the melt-spun membranes are symmetric such that the membranes have a substantially uniform structure throughout the thickness dimension of the membranes, as illustrated in the scanning electron microscope photographs of FIGS. 6 and 7 of a hollow fiber made using such compositions. As defined herein, a "homogeneous" polysulfone membrane is a membrane in which each portion or section of the membrane contributes its substantially proportional share to the permeability characteristics of the membrane.

In an embodiment of the present invention, the membrane comprises: approximately 34 to about 36 weight percent polysulfone; approximately 42 to about 46 weight percent sulfolane; approximately 10 to about 12 weight percent methoxy-PEG (molecular weight approximately 2,000); approximately 1 to about 1.5 weight percent glycerin; approximately 2 to about 3 weight percent polyvinylpyrrolidone; and approximately 4 to about 7 weight percent n-methyl-pyrrolidone.

Polysulfone compounds and their synthesis are well-known in the art. Preferred polysulfone compounds useful in this invention satisfy the formula:

$$R_1\text{---}SO_2\text{---}R_2$$

wherein $R_1$ and $R_2$ (which can be the same or different) are groups such as alkanes, alkenes, alkynes, aryls, alkyls, alkoxys, aldehydes, anhydrides, esters, ethers, and mixtures thereof, each such group having fifty or fewer carbon atoms and including both straight-chained and branched-chained structures. Preferred polysulfone compounds useful in this invention have a melt flow index (MFI) in a range of from about 1.7 dg/min to about 9.0 dg/min as measured according to the American Standard Test Method (ASTM) for Flow Rates of Thermoplastics by Extrusion Plastometer, ASTM D 1238-94a. Goods results have been achieved when the polysulfone compounds have a MFI of from about 2.0 dg/min to about 5.0 dg/min. Preferred polysulfone compounds useful in this invention include, but are not limited to polyarylsulfones, for example, bisphenol A polysulfone, polyether sulfone, polyphenyl sulfone, and mixtures thereof. Especially good results have been achieved utilizing bisphenol A polysulfone.

A "solvent for the polysulfone compound" is defined herein as a compound having the following characteristics: a boiling point of at least about 150° C., a solvating power to dissolve from about 8 weight percent to about 80 weight percent of the polysulfone compound at a temperature in a range from about 50° C. to about 300° C. The solvent preferably can dissolve from about 8 weight percent to about 80 weight percent of a polyarylsulfone.

Candidate solvents useful in this invention include, but are not limited to, tetramethylene sulfone; 3-methyl sulfolane; benzophenone; n,n-dimethylacetamide; 2-pyrrlidone; 3-methylsulfolene; pyridine; thiophene; o-dichlorobenzene; 1-chloronapthalene; methyl salicylate; anisole; o-nitroanisole; diphenly ether; diphenoxy methane; acetophenone; p-methoxyphenyl-2-ethanol; 2-piperidine; antipyrine; diethyl phthalate; diphenyl sulfone; diphenyl sulfoxide; phthalic acid, dioctyl ester; phthalic acid, dimethyl ester; phthalic acid, diethyl ester; phthalic acid, dibutyl ester; phthalic acid, bix(2-ethylhexyl) ester; phthalic acid, benzyl butyl ester; phenyl sulfide. Especially preferred solvents useful in this invention include, but are not limited to, tetramethylene sulfone ("sulfolane"), antipyrine, -valerolactam, diethyl phtalate, and mixtures thereof. Especially good results have been achieved utilizing tetramethylene sulfone as the solvent.

A "non-solvent for the polysulfone compound" is defined herein as a compound having the following characteristics: a boiling point of at least about 150° C., a solvating power sufficiently low to dissolve less than about 5 weight percent of the polysulfone compound at a temperature in a range from about 50° C. to about 300° C.

Candidate non-solvents useful in this invention are 1,1-diethylurea; 1,3-diethylurea; dinitrotoluene; 1,2-ethane diamine; diphenylamine; toluenediamine; o-toluic acid; m-toluic acid; toluene-3,4-diamine; dibutyl phthalate; piperidine; decalin; cyclohexane; cyclohexene; chlorocyclohexane: "cellosolve" solvent; n,n-dimethylbenzylamine; paraffin; mineral oil; mineral wax; tallow amine; triethanol amine; lauryl methacrylate; stearic acid; di(ethylene glycol); tri(ethylene glycol); ethylene glycol; poly(ethylene glycol); tetra(ethylene glycol); glycerin; diethyl adipate; d-sorbitol; chlorotriphenyl stannane; resorcinol; 2-methyl-8-quinolinol; quinaldine; 4-phenylpyridine; phosphorothioic acid, o,o-diethyl o-(p-nitrophenyl) ester; N,N-dimethyl-p-phenylene diamine; 2,6-dimethoxyphenol; 4-allyl-2-methoxyphenol; phenanthridine; 2-naphthylamine; 1-naphthylamine; 1-naphthol; 2-naphthalenethiol; 1-bromonaphthalene; levulinic acid; phenyl pyrrol-2-yl ketone; phenyl 4-pyridyl ketone; isothiocyanic acid, m-nitrophenyl ester; 2-methyl-1H-indole; 4-methyl imidazole; imidazole; 1,7-heptanediol; 9H-fluoren-9-one; ferrocene; 2,2',2"-nitrilotriethanol; 2,2'-iminodiethanol; dibenzofuran; cyclohexaneacetic acid; cyanamide; courmarin; 2,2'-bipyridine; benzoic acid; benzeneproprionic acid; o-dinitrobenzene; 9-methyl-9-azabicyclo(3.3.1)nonan-3-one; chlorodiphenylarsine; antimony bromide; p-anisidine; o-anisaldehyde; adiponitrile; p-amino acetophenone; monoacetin; diacetin; triacetin; pentoxane; 4-benzoylbiphenyl; methyl oleate; triethylphosphate; butyrlacetone; terphenyl; tetradecanol; polychlorinated biphenyl ("Aroclor 1242"); myristic acid; methacrylic acid, dodecyl ester; isocyanic acid, methylenedi-p-phenylene ester; 2-((2-hexyloxy)ethoxy) ethanol; 4-nitro biphenyl; benzyl ether; benzenesulfonyl chloride; 2,4-diisocyanato-1-1-methyl benzene; adipic acid, diethyl ester; 2'-nitro-acetophenone; 1'-acetonaphthone; tetradecanone; (dichlorophenyl)trichlorosilane; dichlorodiphenyl silane; phosphorothioic acid, o,o-diethyl o-(p-nitrophenyl) ester; phosphoric acid, tri-o-tolyl ester; phosphoric acid, triphenyl ester; phosphoric acid, tributyl ester; phenyl phosphorous dichloride; p-nitrophenol; isocyanic acid, methyl-m-phenylene ester; 2,2'-iminodiethanol; N-(2-aminoethyl)-N'-(2-((2-aminoethyl)amino)ethyl) 1,2-ethanediamine; 2,6-di-tert-butyl p-cresol; chloro biphenyl; 4-biphenylamine; benzyl ether; benzenesulfonyl chloride; 1,2(methylenedioxy)-4-propenyl benzene; 2,4-diisocyanato-1-methyl benzene; chlorodinitro benzene (mixed isomers); hexahydro 2H-azepin-2-one; 4,4'-methylenedianiline; 1'-acetonaphthone; mercapto acetic acid; and acetanilide. Especially preferred non-solvents useful in this invention include, but are not limited to, poly(ethylene glycol), di(ethylene glycol), tri(ethylene glycol), glycerol, and mixtures thereof.

The concentrations of the components in the composition may vary and are dependent upon variables many of which can be readily worked out with simple bench experiments. For example, miscibility of the composition at the melt-extrusion temperature is one factor to be considered in determining a suitable component concentration. Miscibility of polysulfone compound solutions can be readily determined empirically by methods known in the art. (Whether or not the components of a composition are miscible is readily apparent.) The end use of the membrane is another factor in determining the appropriate blend composition because the preferred pore size of the membrane and transport rate of liquids and solutes through the membrane vary depending upon the intended fiber end use.

In the case of membranes useful for microfiltration of liquids, the concentration of the polysulfone compound is preferably at least about 8 weight percent, more preferably at least about 12 weight percent. The concentration of the solvent is preferably at least about 40 weight percent, more preferably at least about 60 weight percent. The concentration of the non-solvent, if present, is preferably at least about 1 weight percent, and more preferably at least about 5 weight percent.

In the case of membranes useful for ultrafiltration or dialysis, the concentration of the polysulfone compound is preferably at least about 18 weight percent, more preferably at least about 25 weight percent. The concentration of the solvent is preferably at least about 40 weight percent, more preferably at least about 45 weight percent. Concentration of the non-solvent, if present, is preferably at least about 1 weight percent, more preferably at least about 5 weight percent.

Figure 3:
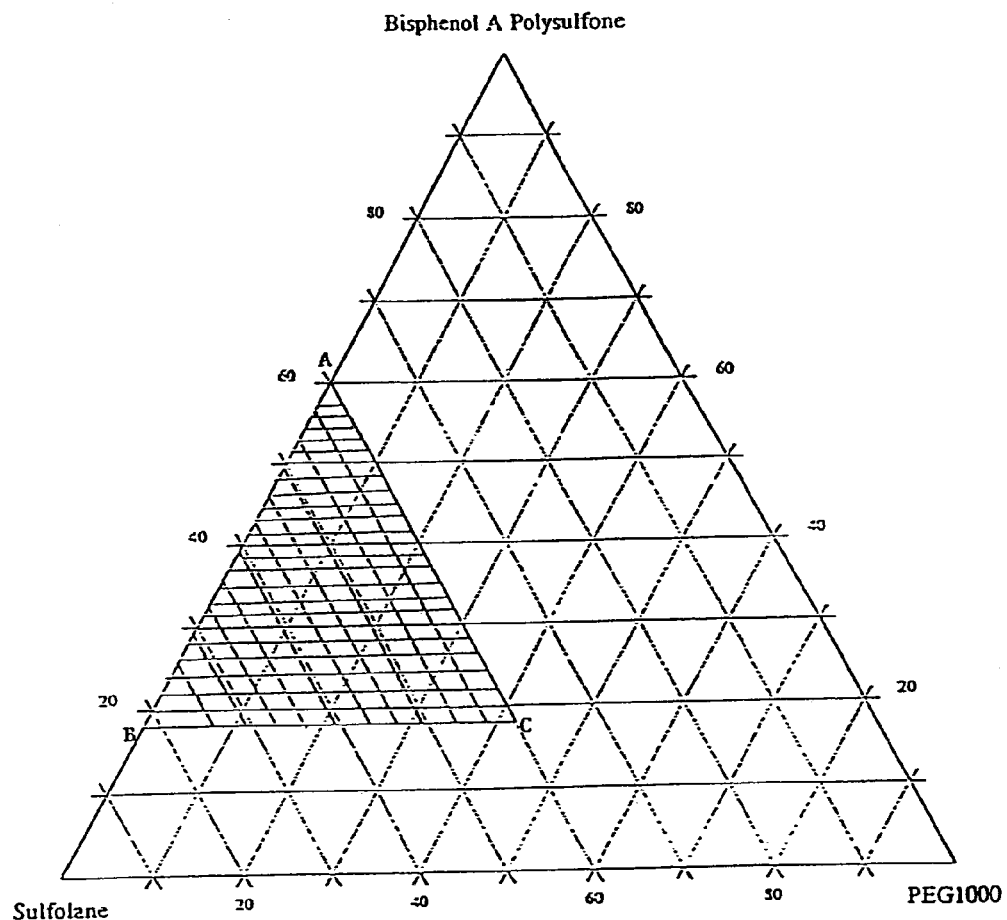
FIG. 3 is a three-component diagram showing the proportions of polysulfone compound, solvent, and non-solvent which are combined in representative melt-spin compositions.

If the non-solvent is present, solvent to non-solvent ratios (i.e., a solvent to non-solvent ratio "sufficient to form a semipermeable membrane useful for liquid separation processes") are preferably about 0.95:1 to about 80:1, and more preferably about 2:1 to about 10:1. For example, as shown in FIG. 3, for a three-component composition (for melt-spinning polysulfone hollow fibers) comprising bisphenol A polysulfone, sulfolane (the solvent), and poly(ethylene glycol) (the non-solvent), acceptable amounts of the polysulfone compound, solvent, and non-solvent lie within the area bounded by the extremes of each component which generate the area A, B, C. Any of the specific compositions consisting of an amount of each of the three components within the area A, B, C of FIG. 3 are suitable for melt spinning into hollow-fiber membranes.

In the case of membranes useful for reverse osmosis of liquids, the concentration of polysulfone is preferably at least about 30 weight percent, more preferably at least about 35 weight percent. The concentration of the solvent is preferably at least about 12 weight percent, more preferably at least about 20 weight percent. If present, the concentration of the non-solvent is preferably at least about 1 weight percent, more preferably at least about 5 weight percent.

Figure 5:
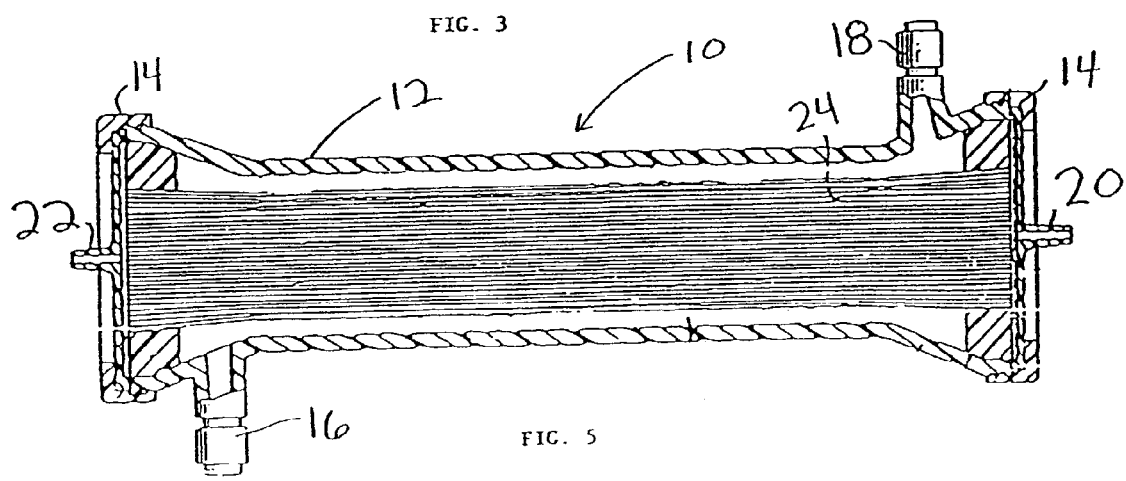
FIG. 5 is a schematic diagram of a hemodialyzer including homogeneous polysulfone hollow-fiber membranes.
Figure 4:
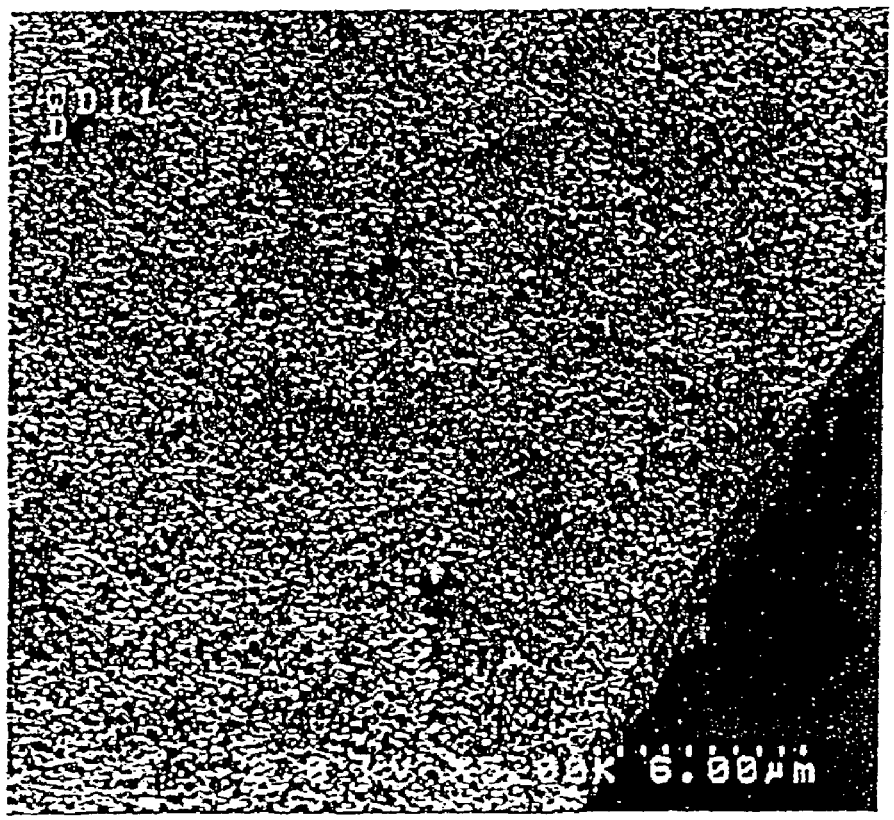
FIG. 4 is a scanning electron microscope photograph of a representative homogeneous, polysulfone hollow fiber.

The compositions of this invention may be used to fabricate polysulfone semipermeable membranes useful for "liquid-separation processes." As defined herein, such processes include, but are not limited to, microfiltration, ultrafiltration, dialysis, and reverse osmosis. FIG. 5 shows a representative liquid-separation device configured for use as an extracorporeal blood treatment device, specifically a hemodialyzer. The hemodialyzer 10 comprises an outer casing 12, end caps 14, a dialysate inlet 16, a dialysate outlet 18, a blood inlet 20, a blood outlet 22, and a bundle of fibers 24 potted in the outer casing. The outer casing defines a dialysate compartment and the lumina of the fibers form a blood compartment. As blood flows through the lumina of the fibers in a parallel fashion, dialysate flows countercurrently through the dialysate compartment.

Figure 2:
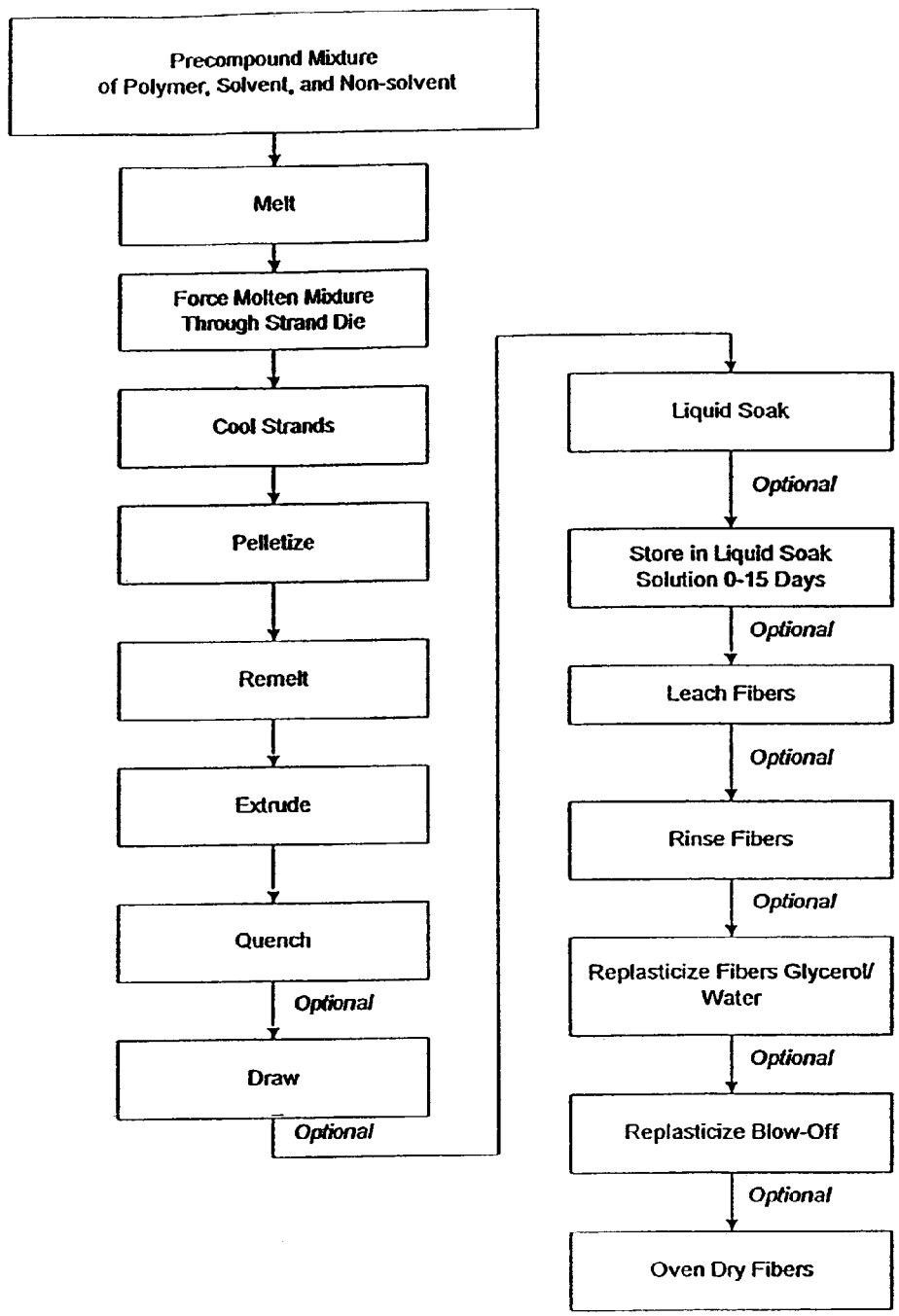
FIG. 2 illustrates an alternative process for fabricating homogeneous polysulfone hollow fibers.

Membranes of the present invention may be fabricated by alternative method schemes as illustrated in FIGS. 1 and 2. A number of method schemes may be followed depending upon the optional method steps chosen to develop the desired polysulfone membrane.

In one preferred method according to the present invention, a polysulfone composition of a UHMW hydrophillic polymer, a polysulfone compound, a solvent, and a non-solvent is precompounded in a high-shear mixer, melted, extruded (as hollow fibers), quenched (FIG. 1), and then wound on cores or reels using any number of commercially available winders, such as Leesona winders. In such a method, adequate care should be taken to maintain a slight tension on the hollow fibers during winding. In another preferred method according to the present invention, the polysulfone composition is precompounded in a high-shear mixer, melted, extruded through a strand die (to form solid strands), cooled, pelletized, remelted, extruded (to form hollow fibers), quenched, and then wound (FIG. 2). In still another preferred method according to the present invention, the polysulfone composition is precompounded, melted, extruded (as hollow fibers), quenched, wound, held dry for a period of time, soaked in a liquid that is substantially a non-solvent for the polysulfone compound and stored in the soaking liquid for up to 15 days (FIG. 1). In yet another preferred method according to the present invention, a polysulfone composition is precompounded in a high-shear mixer, melted, extruded (as hollow fibers), quenched, wound, soaked, leached, rinsed, replasticized, and then dried in an oven (preferably a convection oven) (FIG. 1). In another preferred method according to the present invention, the polysulfone composition is precompounded, melted, extruded (as solid strands), cooled, pelletized, remelted, extruded (as hollow fibers), quenched, wound, and then held dry in air followed by soaking in a liquid that is substantially a non-solvent for the polysulfone compound (FIG. 2). In yet another preferred method according to the present invention, a polysulfone composition is precompounded, melted, extruded (as solid strands), cooled, pelletized, remelted, extruded (as hollow fibers), quenched, wound, soaked, leached, rinsed, replasticized, and dried (FIG. 2).

The components of the composition (i.e., the UHMW hydrophilic polymer, polysulfone compound, solvent, and non-solvent) to be extruded are combined and homogenized prior to extrusion by mixing in a convenient manner with conventional mixing equipment, as for example, a high-shear mixer, such as a compounding twin-screw extruder. The components of the extrusion composition may also be combined and homogenized directly in a meltpot provided with suitable agitation of the molten liquid. Alternatively, a polysulfone extrusion composition may be homogenized by extruding a molten composition through a strand die, cooling the global extrudate, and grinding or pelletizing the extrudate to a particle size readily-fed to a heated, single-screw or twin-screw extruder. Alternatively, other heating/homogenizing methods known to those skilled in the art may be utilized to produce a homogeneous, molten liquid for extrusion (termed a "melt").

The melt is heated to a temperature that facilitates preparation of a homogeneous liquid possessing a viscosity suitable for extrusion. The temperature should not be so high as to cause significant degradation of the polysulfone, the solvent, or the non-solvent. The temperature should not be so low as to render the liquid too viscous for extrusion. For example, when the melt comprises bisphenol A polysulfone, the extrusion temperature is preferably at least about 50° C., more preferably at least about 75° C. The extrusion temperature is preferably less than about 300° C., more preferably less than about 220° C.

The viscosity of the melt should not be so high as to be too viscous to be extruded at temperatures that do not deleteriously affect the polysulfone compound. The viscosity, however, of the melt must not be so low that the extrudate cannot maintain a desired shape upon exiting the extrusion die. The melt may be extruded in a variety of shapes such as, but not limited to, hollow-fibers, tubes, sheets, and hollow-fibers with fins. The extrudate may be aided in retaining its desired shape upon extrusion by cooling.

For making hollow-fiber membranes, the melt is extruded through a hollow-fiber die (spinneret). The spinneret typically is multi-holed and, thus, produces a tow of multiple hollow fibers. The spinneret typically includes a means for supplying a fluid (gas or liquid) to the core or "lumen" of the extrudate. The core fluid is used to prevent collapse of the hollow fibers as they exit the spinneret. The core fluid may be a gas, such as nitrogen, air, carbon dioxide, or other inert gas, or a liquid which is a non-solvent for the polysulfone compound, such as, but not limited to, water, poly(ethylene glycol), di(ethylene glycol), tri(ethylene glycol), glycerol, and mixtures thereof. Mixtures of solvents and non-solvents may be used as long as the mixture is not a solvent for the polysulfone compound. Alternatively, the melt may first be extruded as solid strands through a single or multi-holed strand die and the resulting solid strands cooled and pelletized to a particle size readily fed to a single-screw or twin-screw extruder (FIG. 2). In this alternative method of production, the particles are remelted and then extruded through a single-holed or multi-holed spinneret to form hollow fibers, as described above.

The extrudate exiting extrusion die enters one or more quench zones. The environment of a quench zone may be gaseous or liquid. Within the quench zone, the extrudate is subjected to sufficient cooling to cause gelation and solidification of the membrane. In an embodiment of the method of the present invention, the time period beginning after the extrudate exits the die and extending to before the membrane is wound onto a core or reel, is important to attain the desired permeability of the membrane. During this time period, for a given composition, the permeability of the membrane is determined largely by the cooling rate to which the extrudate is subjected. Permeability is increased by rapid quenching of the extrudate, compared to the permeability obtained from a less drastic quench or slower gelling of the extrudate. Increasing permeability of the membranes, which results from more rapid quenching, normally affects the ability of the membranes to transport water, or other liquids and compounds across the thickness dimension of the membranes. Thus, the extrudate cooling rate (as affected by the temperature and composition of the cooling medium employed) may be varied to modify the permeability of the resulting membrane.

In one method according to the present invention, a polysulfone hollow-fiber extrudate is quenched in air. Within the quench zone, the hollow fibers gel and solidify. The temperature of the air-quench zone is preferably less than about 27° C., more preferably less than about 24° C. The hollow fibers are held in the air zone for preferably less than about 180 minutes, more preferably less than about 30 minutes.

In another preferred method according to the present invention, the hollow-fiber extrudate is quenched in a liquid that is substantially a non-solvent for the polysulfone compound, such as water, poly(ethylene glycol), di(ethylene glycol), tri(ethylene glycol), glycerol, or a mixture thereof. A mixture of solvent(s) and non-solvent(s) alternatively may be used so long as the mixture remains substantially a non-solvent for the polysulfone compound. When a liquid quench comprises water and one or more other components, the ratio of water to the other components is preferably from about 0.25:1 to about 200:1. The temperature of the liquid quench zone is preferably less than about 50° C., more preferably less than about 25° C., and more preferably less than about 10° C. The advantage of a liquid quench is that it offers less resistance to the transfer of heat from the extrudate to the cooling medium than is present in an air quench and, thus, results in a more rapid removal of heat from the extrudate as the membrane forms. The rapid removal of heat modifies the permeability of the resulting membrane and can be used to tailor membrane permeability for the intended end use.

Hollow fibers are, optionally, drawn using godet rollers or other conventional equipment to the appropriate fiber diameter. More specifically, drawing or stretching the fiber may be accomplished by passing the hollow fiber over a series of rollers. The desired degree of stretching may be obtained by control of the rate of rotation of the second roller or second group of rollers relative to the first roller encountered by the fiber. Line speeds are generally not critical and may vary over a wide range. Preferred line speeds are at least about 10 feet per minute and less than about 1000 feet per minute.

In another preferred method according to the present invention, as illustrated in FIG. 2, following quenching, the membrane is passed through at least one leach bath containing a liquid that is substantially a non-solvent for the polysulfone compound, such as water or a mixture of water and sulfolane and/or the non-solvent(s), or a mixture of water and the solvent utilized in the melt composition. Good results have been achieved when the leach bath is water. The membrane is leached to remove at least a portion of the solvent and the non-solvent. The leach bath need not remove all of the solvent and non-solvent from the membrane, depending, at least in part, on the anticipated end use of the membrane.

The minimum temperature of the leach bath is such that removal of the solvent and non-solvent from the membrane occurs at a reasonable rate relative to production rate demands. The minimum temperature of the leach bath is preferably at least about 20° C., more preferably at least about 40° C. The maximum temperature of the leach bath is below a temperature at which the integrity of the membrane is deleteriously affected. Accordingly, the temperature of the leach bath is preferably less than about 95° C.

By way of example, the residence time of a hollow-fiber membrane in the leach bath is preferably less than about 1200 seconds, more preferably less than about 300 seconds. The hollow fiber may, optionally, be drawn to the desired size prior to entrance into the leach bath, during the residence time in the leach bath, subsequent to exiting the leach bath, or during any combination thereof.

Following immersion in the leach bath, the membrane may, optionally, be passed through a rinse bath containing water. The rinse bath removes residues in the membrane from the leach process. The rinse bath is preferably maintained at room temperature. For a hollow fiber, the residence time of the fiber within the rinse bath is preferably less than 1200 seconds, more preferably less than 300 seconds.

After leaching, the membrane may then be subjected to a replasticization process. For hollow-fiber membranes to be used for dialysis, a replasticization bath is used that preferably contains less than about 50 weight percent glycerol and more preferably less than about 45 weight percent glycerol, with the balance being water. The minimum temperature of the replasticization bath is such that replasticization of the membrane occurs at reasonable rate relative to production demands. For example, the minimum temperature of a glycerol-containing replasticization bath is preferably at least about 20° C., more preferably at least about 35° C. The maximum temperature of the replasticization bath is below a temperature at which the membrane integrity could be adversely affected. Accordingly, the maximum temperature of the replasticization bath is preferably less than about 100° C., more preferably less than about 50° C.

Following removal of the membrane from the replasticization bath, excess liquid adhering to the membrane may optionally be removed, preferably by use of a conventional air knife operating at a pressure of about 10 psig to about 60 psig. With hollow fibers, good results have been achieved when the air knife is maintained at a pressure of about 30 psig.

The resulting polysulfone membrane may, optionally, be dried in an oven (preferably a convection oven). The oven is maintained at a temperature of from about 20° C. to about 200° C. With hollow fibers, good results have been achieved when the temperature of the oven is about 70° C. In a convection oven the membrane is dried for a period of from about 5 seconds to about 1200 seconds. With hollow fibers, goods results have been achieved when the fiber was dried for at least about 140 seconds.

The semipermeable polysulfone membranes formed by the described methods may be used in liquid-separation processes such as, but not limited to, microfiltration, ultrafiltration, dialysis, and reverse osmosis. The specific fabrication method that is employed, within the scope of methods according to the present invention, is selected so as to tailor the resulting membrane for its anticipated end use. Such adaption is readily achieved by one skilled in the art based upon the teachings herein.

By way of example and not limitation, examples of the invention will now be given.

EXAMPLE 1

A composition was prepared comprising about 36 weight percent Udel P1835NT11, a brand of bisphenol A polysulfone (available from Amoco Polymers, Inc. of Alpharetta, Ga.) about 44.3 weight percent anhydrous sulfolane (available from Phillips Chemical Company of Borger, Tex.) and about 17.7 weight percent poly(ethylene glycol) having an average molecular weight of about 1000 daltons (available from Dow Chemical Company of Midland, Mich.). The solvent to non-solvent ratio was about 2.5:1. The composition was compounded in a co-rotating twin-screw extruder at about 132° C. The extruded composition was cooled, pelletized using an RCP 2.0 pelletizer (available from Randcastle Extrusion Systems, Inc. of Cedar Grove, N.J.), and then remelted and extruded through a 30-hole hollow-fiber spinneret at about 149° C. using a single-screw extruder. The resulting hollow-fiber extrudate was quenched in air at about 21° C. for about 15 seconds, drawn from a first godet (rotating at a surface speed of 172 feet per minute) to a second godet (rotating at a surface speed of 182 feet per minute) to increase the fiber's length by about 5.75 percent, wound on a core, and soaked in a water bath at a temperature of about 25° C. for about four hours.

Following soaking in water, the hollow fiber was processed by unwinding the fiber from the core at a rate of about 30 ft/min and passing the fiber through a 37° C. water bath for about 40 seconds. The fiber was then immersed in a room temperature water-rinse bath for 139 seconds. Following the rinse bath, the fiber was replasticized by immersion for 140 seconds in a 40-percent aqueous glucerol replasticization bath held at about 37° C. After removing the fiber from the aqueous glycerol bath, excess liquid was removed from the fiber using an air knife operating at about 30 psig. The processed hollow fiber was then dried in a convection oven at about 70° C. for 155 seconds.

The resulting hollow fiber had an average lumen diameter of 160 μm, and an average wall thickness of 18 μm. The hollow fiber was fabricated into a dialysis test unit containing 150 fibers. The in vitro water flux of the device was 102.5 mL/(hr·mmHg·m$^2$) and the average $K_{ov}$ for sodium chloride was found to be $1.92 \times 10^{-2}$ centimeters per minute at a solution flow rate through the fiber lumina of about 0.02 milliliters per minute per fiber. $K_{ov}$ is defined in the following equation:

$$\frac{1}{K_{ov}} = \frac{1}{K_b} + \frac{1}{P_m}$$

where $K_b$ is the resistance to mass transfer within the fluid present in the lumen of the hollow fiber, and $P_m$ is the membrane permeability. It was not possible to determine the membrane permeability, $P_m$, alone using the test apparatus because the flow of solution through an individual fiber could not be made large enough to render $K_b$ negligible.

This hollow-fiber membrane could be fabricated into a suitable device for use as an ultrafiltration cell for the removal of contaminants from water of aqueous solutions.

EXAMPLE 2

A composition was prepared comprising about 36 weight percent Udel P1835NT11 polysulfone (Amoco Polymers, Inc.), about 45.7 weight percent anhydrous sulfolane (Phillips Chemical), and about 18.3 weight percent poly(ethylene glycol) having an average molecular weight of about 1000 daltons (Dow Chemical), yielding a solvent to non-solvent ratio about 2.5:1. The composition was compounded in a co-rotating, twin-screw extruder at about 173° C. The extruded composition was then pelletized, remelted, and extruded through a 30-hole hollow-fiber spinneret at about 178° C. using a single-screw extruder. The resulting hollow-fiber extrudate was quenched in air at about 22° C. for 7–8 seconds. The resulting hollow-fiber membrane was wound on a core at about 110 feet per minute, and held dry for about one hour. The hollow fiber was then placed in a water bath maintained at a temperature of about 25° C. for a period of about 12–15 hours.

The hollow fiber was then processed by unwinding the fiber from the core at about 30 ft/min and passing the fiber through a 36° C. water leach bath for about 40 seconds. The fiber was immersed in a room temperature water-rinse bath for 139 seconds. The fiber was replasticized for 140 seconds in a 37° C. bath of about 40 weight percent aqueous glycerol. After removing the fiber from the aqueous glycerol bath, excess liquid was stripped from the fiber using an air knife operating at a pressure of about 30 psig. The processed fiber was then dried in a convection oven at about 70° C. for 155 seconds.

The resulting hollow fiber had an average lumen diameter of about 142 μm and an average wall thickness of about 31 μm. Dialysis test units each containing 150 of the hollow fibers were fabricated. The average in vitro water flux of these devices was 68.0 mL/(hr·mmHg·m$^2$) and the average $K_{ov}$ for sodium chloride was about $2.28 \times 10^{-2}$ centimeters per minute at a solution flow rate through the fiber lumina of about 0.02 milliliters per minute per fiber. This hollow-fiber membrane is useful for ultrafiltration, such as for use in an ultrafiltration cell for the removal of contaminants from water or aqueous solutions.

EXAMPLE 3

A composition was prepared comprising about 38 weight percent Udel P1835NT11 polysulfone (Amoco Polymers, Inc.), about 44.3 weight percent anhydrous sulfolane (Phillips Chemical), and about 17.7 weight percent poly(ethylene glycol) having an average molecular weight of about 1000 daltons (Dow Chemical), yielding a solvent to non-solvent ratio about 2.5:1. The composition was compounded in a co-rotating, twin-screw extruder at about 99° C., and extruded directly through a 30-hole hollow-fiber spinneret. The extrudate was quenched in air at about 26° C. for about 6 seconds. The resulting hollow-fiber membrane was wound on a core at about 160 feet per minute, and placed immediately into a water bath for a period of about 12–15 hours.

The hollow fiber was then unwound from the core at about 30 ft/min and passed through a 37° C. water leach bath for about 40 seconds. The fiber was then immersed in a room temperature water-rinse bath for about 140 seconds. The fiber was replasticized for 140 seconds in an aqueous glycerol bath containing about 40 weight percent glycerol, the bath being held at about 38° C. After removing the fiber from the aqueous glycerol bath, excess liquid was removed from the fiber by an air knife operating at a pressure of about 30 psig. The fiber was then dried in a convection oven at about 70° C. for about 155 seconds.

The resulting hollow-fiber membrane had an average lumen diameter of about 237 μm, and an average wall thickness of about 35 μm. Dialysis test units each containing 150 of the resulting fibers were fabricated from this fiber. The average in vitro water flux of these devices was 143.5 mL/(hr·mmHg·m$^2$) and the average $K_{ov}$ for sodium chloride was found to be 0.88×10$^{-2}$ centimeters per minute at a solution flow rate through the fiber lumina of about 0.02 milliliters per minute per fiber. This hollow-fiber membrane can be used in an ultrafiltration cell for the removal of contaminants from water or aqueous solutions.

EXAMPLE 4

A composition was prepared comprising about 38 weight percent Udel P1835NT11 polysulfone (Amoco Polymers, Inc.), about 45.7 weight percent anhydrous sulfolane (Phillips Chemical), and about 18.3 weight percent poly(ethylene glycol) having an average molecular weight of about 1000 daltons (Dow Chemical), yielding a solvent to non-solvent ratio about 2.6:1. The composition was compounded in a co-rotating, twin-screw extruder at about 143° C., and extruded directly through a 30-hole hollow-fiber spinneret. The extrudate was quenched in air at about 25° C. for about 0.08 minutes, wound on a core at about 203 feet per minute, and held dry for thirty minutes before being placed in a 25° C. water bath for about three days.

The hollow fiber was then unwound from the core at about 30 ft/min and passed through a 38° C. water leach bath for about 30 seconds. The fiber was immersed in a room temperature water-rinse bath for 148 seconds. The fiber was replasticized for 149 seconds in an aqueous glycerol bath containing about 40 weight percent aqueous glycerol, the bath being held at about 38° C. After removing the fiber from the aqueous glycerol bath, excess liquid was removed from the fiber using an air knife operating at a pressure of about 30 psig. The processed hollow fiber was dried in a convection oven at about 70° C. for 147 seconds.

The resulting hollow fiber membrane had an average lumen diameter of about 192 μm, and an average wall thickness of about 29.5 μm. Dialysis test units each containing 150 of the resulting fibers were fabricated. The average in vitro water flux of these devices was 141.2 mL/(hr·mmHg·m$^2$) and the average $K_{ov}$ for sodium chloride was found to be 1.20×10$^{-2}$ centimeters per minute at a solution flow rate through the fiber lumina of about 0.02 milliliters per minute per fiber. This hollow-fiber membrane is useful in an ultrafiltration cell for the removal of contaminants from water or aqueous solutions.

EXAMPLE 5

A composition was prepared comprising about 34 weight percent Udel P1835NT11 polysulfone (Amoco Polymers, Inc.), about 54 weight percent anhydrous sulfolane (Phillips Chemical), about 12 weight percent poly(ethylene glycol) having an average molecular weight of about 1000 daltons (Dow Chemical), and about 1 weight percent glycerol (Van-Waters & Rogers, Inc., Seattle, Wash.), yielding a solvent to non-solvent ratio about 4.5:1. The composition was compounded in a co-rotating, twin-screw extruder at about 144° C. The extrudate was then cooled, pelletized, remelted, and extruded through a 30-hole hollow-fiber spinneret at about 134° C. using a single-screw extruder. The resulting extrudate was quenched in air at about 20° C. for 0.08 minute, and wound on a core at about 200 feet per minute. The entire wound core was immediately placed in a 25° C. water bath for a period of about 15–20 hours.

The hollow fiber was then processed by unwinding the fiber from the core at about 30 ft/min and passing the fiber through a room-temperature water-leach bath for 97 seconds. The fiber was replasticized for 145 seconds in a bath containing about 40 weight percent aqueous glycerol held at about 38° C. After removing the fiber from the aqueous glycerol bath, excess liquid was stripped from the fiber using an air knife operating at a pressure of about 30 psig. The processed hollow fiber was dried in a convection oven at about 62° C. for 151 seconds.

The resulting hollow-fiber membrane had an average lumen diameter of about 165 μm, and an average wall thickness of about 18 μm. Test units each containing about 150 of the resulting fibers were fabricated. The average in vitro water flux of these devices was 67.2 mL/(hr·mmHg·m$^2$) and the average $K_{ov}$ for sodium chloride was found to be 2.19×10$^{-2}$ centimeters per minute at a solution flow rate through the fiber lumina of about 0.02 milliliters per minute per fiber.

EXAMPLE 6

A composition was prepared comprising about 34 weight percent Udel P1835NT11 polysulfone (Amoco Polymers, Inc.), about 54 weight percent anhydrous sulfolane (Phillips Chemical), about 6 weight percent poly(ethylene glycol) having an average molecular weight of about 1000 daltons (Dow Chemical), and about 6 weight percent tri(ethylene glycol) (Aldrich Chemical Company, Inc., Milwaukee, Wis.), yielding a solvent to non-solvent ratio about 9:1. The composition was compounded in a co-rotating, twin-screw extruder at about 153° C. The extrudate was then cooled, pelletized, remelted, and extruded through a 30-hole hollow-fiber spinneret at about 137° C. using a single-screw extruder. The resulting hollow-fiber extrudate was quenched in air at about 20° C. for 0.08 minute, and wound on a core at about 200 feet per minute. The entire fiber core was immediately placed in a 25° C. water bath for a period of 15–20 hours.

The hollow fiber was then processed by unwinding the fiber from the core at about 30 ft/min and passing the fiber through a room-temperature water-leach bath for 95 seconds. The fiber was then immersed in a room temperature water-rinse bath for 134 seconds. The hollow fiber was replasticized for 146 seconds in a bath of about 40 weight percent aqueous glycerol held at about 38° C. After removing the fiber from the aqueous glycerol bath, excess liquid was stripped from the fiber using an air knife operating at a pressure of about 30 psig. The processed fiber was dried in a convection oven at about 70° C. for 150 seconds.

The resulting hollow-fiber membrane had an average lumen diameter of about 180 μm, and an average wall thickness of about 20 μm. Test units each containing about 150 of the resulting fibers were fabricated. The average in vitro water flux of these devices was 60.0 mL/(hr·mmHg·m$^2$) and the average $K_{ov}$ for sodium chloride was found to be $2.17 \times 10^{-2}$ centimeters per minute at a solution flow rate through the fiber lumina of about 0.02 milliliters per minute per fiber.

EXAMPLE 7

A composition was prepared comprising about 32 weight percent Udel P1835NT11 polysulfone (Amoco Polymers, Inc.), about 53 weight percent anhydrous sulfolane (Phillips Chemical), and about 15 weight percent poly(ethylene glycol) having an average molecular weight of about 1000 daltons (Dow Chemical), yielding a solvent to non-solvent ratio about 3.5:1. The composition was compounded in a co-rotating twin-screw extruder at about 131° C. and extruded directly through a 30-hole hollow-fiber spinneret. The extrudate was quenched in water at about 7° C. for about 6 seconds. The resulting hollow-fiber membranes were wound on a core at about 244 feet per minute. The entire fiber core was immediately placed in a 25° C. water bath for a period of about 15–20 hours.

The hollow fibers were then processed by unwinding the fibers from the core at about 30 ft/min and passing the fibers through a room-temperature water-leach bath for 97 seconds. The fibers were then immersed in a room temperature water-rinse bath for 135 seconds. The fibers were replasticized for 146 seconds in a bath of about 40 weight percent aqueous glycerol, the bath being held at about 38° C. After removing the fibers from the aqueous glycerol bath, excess liquid was stripped from the fiber using an air knife operating at a pressure of about 20 psig. The processed fibers were dried in a convection oven at about 45° C. for 152 seconds.

The resulting hollow-fiber membranes had an average lumen diameter of about 203 μm, and an average wall thickness of about 37 μm. Test units each containing about 150 of the resulting fibers were fabricated. The average in vitro water flux of these devices was 9.1 mL/(hr·mmHg·m$^2$) and the average $K_{ov}$ for sodium chloride was found to be $1.76 \times 10^{-2}$ centimeters per minute at a solution flow rate through the fiber lumina of about 0.02 milliliters per minute per fiber.

EXAMPLE 8

Performance of membranes were determined in vitro based on AMMI and EN123 guidelines applicable to hemodialyzers as of following:

1. Small solute clearance:

The clearances of urea, creatinine, and phosphate are determined using open loop circuit at following conditions:
Blood inlet flow rate, $Q_{Bin}$=300 ml/min
Dialysate inlet flow rate, Qd=500 ml/min
Ultrafiltration flow rate, Qf=10 ml/min
The concentrations of solute in solution were as follows:
Urea=1.0 g/l
Creatinine=0.2 g/l
Phosphate=0.12 g/l
The clearance was calculated by means of the expression:

$$\text{Clearance(ml/min)} = Q_{Bin}(C_{Bin}-C_{Bout})/C_{Bin} + Qf(C_{Bout}/C_{Bin})$$

Where $C_{Bin}$ and $C_{Bout}$ are the concentration of solute at blood inlet and outlet.

2. Middle molecule solute clearance

Middle solute clearances such as vitamin B12, and cytochrome-C were determined using closed loop circuit at the same flow rates as in the case of small solute clearance with the solute concentration in the range of 300 to 500 ppm. The clearance was calculated as follows:

$$\text{Clearance(ml/min)} = Qf[(BT/ln(1-QfT/V)+1]$$

Where
B=slope of the regression analysis of the time elapsed and the natural logarithm of the concentration of the test solution
T=elapsed time
V=volume of the reservoir at time zero
Qf=ultrafiltration rate 3. Albumin sieving coefficient and ultrafiltration rate was calculated as follows:

Bovine serum is used in these tests. The total protein content is 60±5 g/l. Bovine serum is recirculated through the blood compartment at Qb=300 ml/min and Qf=60 ml/min, while there is no fluid circulating through other compartment. The ultrafiltration rate, Kuf is determined after 1 hour recirculation at Qf=60 ml/min. The slope of Qf versus the trans membrane pressure, (TMP–mmHg) is used for the computation of Kuf.

$$Kuf = (Qf \times 60)/TMP, \; ml/h/mmHg$$

The albumin sieving coefficient, S is obtained by means of the expression:

$$S = 2Cp/(C_{Bin}+C_{Bout})$$

Where Cp is the concentration of solute in the ultrafiltrate.

4. Platelet drop was determined as follows:

Fresh bovine blood is used in this test. The dialyzers, including membranes, to be tested for platelet drop are primed with IL of saline solution then attached to the dialyzer into the test system as shown in FIG. 8. 500 ml of blood maintained at 37±1° C. was used for each test. Blood was recirculated at 300 ml/min with closed dialysate ports. Blood samples, 1 ml each, were collected at 0, 1, 15, 30, 60, 90, 120, and 180 minutes for platelet counts by means of a Coulter Differential Cell Counter. The average value of two readings was used to assess the platelet variation versus recirculation time.

EXAMPLE 9

By way of example, polysulfone fiber A was spun from a formulation consisting of:
Polysulfone=37.6%
Polyethylene glycol (MW=1,000 daltons)=11.0 wt %
Sulfolane=49.2 wt %
Glycerin=1.2 wt %
Polyvinylyrrolidone (UHMW)=1.0 wt %

To this end, a composition was prepared comprising about 37.6 weight percent Udel polysulfone, about 49.2 weight percent anhydrous sulfolane, about 11.0 weight percent polyethylene glycol, about 1.2 weight percent glycerin, and about 1.0% UHMW polyvinylpyrrolidone. The composition was compounded in a co-rotating, twin screw extruder about 160° C., and then extruded through a 16-hole hollow fiber spinneret at about 145° C. The extrudate was quenched in the air at about 18° C. for about 30 seconds. The resulting hollow-fiber membrane was wound on a core at about 200 m/min, after being passed through a water bath at about 37° C. for about 10 seconds.

The hollow fiber membrane was then unwound from the core at about 60 ft/min and passed through a 40° C. water bath for about 150 seconds. The fiber was replasticized for about 30 seconds in an aqueous glycerol bath containing about 40 weight percent glycerol, the bath temperature was about 38° C. After removing the fiber from the aqueous glycerin bath, excess liquid was removed from the fiber by an air knife operating at a pressure of about 12 psig. The fiber was then dried in a convection oven at about 70° C. for about 200 seconds and wound on a core at about 60 ft/min.

The obtained fiber shows a symmetric structure as illustrated in FIGS. 6 and 7. Fiber dimension and functional performance is given in Table I below. In-vitro platelet results tested with bovine blood are shown in FIG. 9. There was no drop in platelet after 3 hours of recirculation.

EXAMPLE 10

By way of example, polysulfone fiber B was spun from a formulation consisting of:

Polysulfone=36.0%
Polyethylene glycol (MW=1,000 daltons)=11.5 wt %
Glycerin=1.3 wt %
Sulfolane=51.2 wt %
Without Polyvinylpyrrolidone (UHMW)=0 wt %

To this end, a composition was prepared comprising about 36.0 weight percent Udel polysulfone, about 51.2 weight percent anhydrous sulfolane, about 11.5 weight percent polyethylene glycol, and about 1.3 weight percent glycerin. The composition was compounded in a co-rotating, twin screw extruder about 160° C., and then extruded through a 16-hole hollow fiber spinneret at about 145° C. The extrudate was quenched in the air at about 18° C. for about 30 seconds. The resulting hollow-fiber membrane was wound on a core at about 200 m/min, after being passed through a water bath at about 37° C. for about 10 seconds.

The hollow fiber membrane was then unwound from the core at about 60 ft/min and passed through a 40° C. water bath for about 150 seconds. The fiber was replasticized for about 30 seconds in an aqueous glycerol bath containing about 40 weight percent glycerol, the bath temperature was about 38° C. After removing the fiber from the aqueous glycerin bath, excess liquid was removed from the fiber by an air knife operating at a pressure of about 12 psig. The fiber was then dried in a convection oven at about 70° C. for about 200 seconds and wound on a core at about 60 ft/min.

The obtained fiber shows a symmetric structure as illustrated in FIGS. 6 and 7. Fiber dimension and functional performance is given in Tables I and II. In-vitro platelet results using bovine blood are shown in FIG. 9. The platelet reduction was approximately 40% after 3 hours of recirculation.

EXAMPLE 11

By way of example, polysulfone fiber C was spun from a formulation consisting of:

Polysulfone=36.0%
Methyl-polyethylene glycol (MW=2,000 daltons)=11.0 wt %
Sulfolane—44.2 wt %
Glycerin—1.3 wt %
Polyvinylpyrrolidone (UHMW) 2.5 wt %
N-Methyl-pyrrolidone=5.0 wt %

To this end, a composition was prepared comprising about 36.0 weight percent Udel polysulfone, about 44.2 weight percent anhydrous sulfolane, about 11.0 weight percent polyethylene glycol, about 1.3 weight percent glycerin, 5.0 weight percent NMP, and about 2.5% UHMW polyvinylpyrrolidone. The composition was compounded in a co-rotating, twin screw extruder about 160° C., and then extruded through a 16-hole hollow fiber spinneret at about 145° C. The extrudate was quenched in the air at about 18° C. for about 30 seconds. The resulting hollow-fiber membrane was wound on a core at about 200 m/min, after being passed through a water bath at about 37° C. for about 10 seconds.

The hollow fiber membrane was then unwound from the core at about 60 ft/min and passed through a 40° C. water bath for about 150 seconds. The fiber was replasticized for about 30 seconds in an aqueous glycerol bath containing about 40 weight percent glycerol, the bath temperature was about 38° C. After removing the fiber from the aqueous glycerin bath, excess liquid was removed from the fiber by an air knife operating at a pressure of about 12 psig. The fiber was then dried in a convection oven at about 70° C. for about 200 seconds and wound on a core at about 60 ft/min.

The obtained fiber shows a symmetric structure as illustrated in FIGS. 6 and 7. Fiber dimension and functional performance is given in Tables I and II. In-vitro platelet results tested with bovine blood are shown in FIG. 9. There was no drop in platelet after 3 hours of recirculation.

EXAMPLE 12

By way of example, polysulfone fiber D was spun from a formulation consisting of:

Polysulfone=35.0%
Methyl-polyethylene glycol (MW=2,000 daltons)=11.0 wt %
Sulfolane=43.2 wt %
Glycerin=1.2 wt %
Polyvinylpyrrolidone (UHMW)=2.1 wt %
N-Methyl-pyrrolidone=7.2 wt %

To this end, a composition was prepared comprising about 35.0 weight percent Udel polysulfone, about 43.2 weight percent anhydrous sulfolane, about 11.0 weight percent polyethylene glycol, about 1.2 weight percent glycerin, 7.2 weight percent NMP, and about 2.1% UHMW polyvinylpyrrolidone. The composition was compounded in a co-rotating, twin screw extruder about 160° C., and then extruded through a 16-hole hollow fiber spinneret at about 145° C. The extrudate was quenched in the air at about 18° C. for about 30 seconds. The resulting hollow-fiber membrane was wound on a core at about 200 nm/min, after passed through a water bath at about 37° C. for about 10 seconds.

The hollow fiber membrane was then unwound from the core at about 60 ft/min and passed through a 40° C. water bath for about 150 seconds. The fiber was replasticized for about 30 seconds in an aqueous glycerol bath containing about 40 weight percent glycerol, the bath temperature was about 38° C. After removing the fiber from the aqueous glycerin bath, excess liquid was removed from the fiber by an air knife operating at a pressure of about 12 psig. The fiber was then dried in a convection oven at about 70° C. for about 200 seconds and wound on a core at about 60 ft/min.

The obtained fiber shows a symmetric structure as illustrated in FIGS. 6 and 7. Fiber dimension and functional performance is given in Tables I and II. In-vitro platelet results tested with bovine blood are shown in FIG. 9. There was no drop in platelet after 3 hours of recirculation.

Data in FIG. 9 and Table II suggests that the use of a small amount of UHMW hydrophilic polymer, Polyvinylpyrrolidone in formulation resulted in a non-thrombogenic polysulfone fiber suitable for dialysis application.

TABLE I

Specification and Functional Performance of Polysulfone Fiber

| Polysulfone Fiber | Fiber ID, micron | Fiber Wall, micron | Water Permeability, ml/h/m2/mmHg | Strength at break, g/cm2 |
|---|---|---|---|---|
| Fiber A | 197 | 20 | 44 | 550,000 |
| Fiber B | 192 | 25 | 23 | 441,000 |
| Fiber C | 184 | 21 | 38 | 430,000 |
| Fiber D | 189 | 22 | 50 | 324,000 |
| Fresenius F60B | 199 | 42 | 35 | 85,000 |

TABLE II

| | | In-vitro Performance | | | | | | |
|---|---|---|---|---|---|---|---|---|
| | Surface | Solute clearance, ml/min | | | | | | |
| Polysulfone | (m2) | Urea | Creatinine | Phosphate | B12 | Cyt-C | Kuf | Alb S.C. |
| Fiber B | 1.9 | 231 | 204 | 182 | 102 | 43 | 22 | 0.01 |
| Fiber C | 1.6 | 236 | 203 | 186 | 107 | 45 | 7.8 | 0.01 |
| Fiber D | 2.6 | 275 | 251 | 240 | 191 | 115 | 14.6 | 0.02 |

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A melt-spun polysulfone semipermeable membrane, the polysulfone semipermeable membrane comprising a mixture of:
   an ultra-high-molecular-weight hydrophilic polymer, greater than 35 percent by weight to about 38 percent by weight of a polysulfone compound, and a solvent for the polysulfone compound, the polysulfone semipermeable membrane having a homogeneous structure such that the polysulfone semipermeable membrane has a substantially uniform structure throughout a thickness of the melt-spun polysulfone semipermeable membrane.

2. The polysulfone semipermeable membrane of claim 1, wherein the ultra-high-molecular-weight hydrophilic polymer is polyvinylpyrrolidone.

3. The polysulfone semipermeable membrane of claim 1, wherein the polysulfone compound is selected from the group consisting of bisphenol A polysulfone, polyether polysulfone, polyphenyl polysulfone, and mixtures thereof.

4. The polysulfone semipermeable membrane of claim 1, wherein the ultra-high-molecular-weight hydrophilic polymer has a molecular weight of approximately 1,000,000 to about 1,500,000 daltons.

5. The polysulfone semipermeable membrane of claim 4, wherein the non-solvent is selected from the group consisting of 1,1-diethylurea, 1,3-diethylurea, dinitrotoluene, 1,2-ethane diamine, diphenylamine, toluenediamine, o-toluic acid, m-toluic acid, toluene-3,4-diamine, dibutyl phthalate, piperidine, decalin, cyclohexane, cyclohexene, chlorocyclohexane, cellosolve solvent, n,n-dimethylbenzylamine, paraffin, mineral oil, mineral wax, tallow amine, triethanol amine, lauryl methacrylaate, stearic acid, di(ethylene glycol), tri(ethylene glycol), ethylene glycol, poly(ethylene glycol), tetra(ethylene glycol), glycerin, diethyl adipate, d-sorbitol, chlorotriphenyl stannane, resorcinol, 2-methyl-8-quinolinol, quinaldine, 4-phenylpyridine, phosphorothioic acid, o,o-diethyl o-(p-nitrophenyl) ester, N,N-dimethyl-p-phenylene diamine, 2,6-dimethoxyphenol, 4-allyl-2-methoxyphenol, phenanthridine, 2-naphthylamine, 1-naphthylamine, 1-naphthol, 2-naphthalenethiol, 1-bromonaphthalene, levulinic acid, phenyl pyrrol-2-yl ketone, phenyl 4-pyridyl ketone, isothiocyanic acid, m-nitrophenyl ester, 2-methyl-1H-indole, 4-methyl imidazole, imadazole, 1,7-heptanediol, 9H-fluoren-9-one, ferrocene, 2,2',2"-nitrilotriethanol, 2,2"-iminodiethanol, dibenzofuran, cyclohexaneacetic acid, cyanamide, courmarin, 2,2'-bipyridine, benzoic acid, benzenepropionic acid, o-dinitrobenzene, 9-methyl-9-azabicyclo(3.3.1)nonan-3-one, chlorodiphenylarsine, antimony bromide, p-anisidine, o-anisaldehyde, adiponitrile, p-amino acetophenone, monoacetin, diacetin, triacetin, pentoxane, 4-benzoylbiphenyl, methyl oleate, triethylphosphate, butyrolactone, terphenyl, tetradecanol, polychlorinated biphenyl, myristic acid, methacrylic acid, dodecyl ester, isocyanic acid, methylenedi-p-phenylene ester, 2-((2-hexyloxy)ethoxy) ethanol, 4-nitro biphenyl, benzyl ether, benzenesulfonyl chloride, 2,4-diisocyanato-1-1-methyl benzene, adipic acid, diethyl ester, 2'-nitro-acetophenone, 1'-acetonaphthone, tetradecanone, (dichlorophenyl)trichlorosilane, dichlorodiphenyl silane, phosphorothioic acid, o,o-diethyl o-(p-nitrophenyl) ester, phosphoric acid, tri-tolyl ester, phosphoric acid, triphenyl ester, phosphoric acid, tributyl ester, phenyl phosphorous dichloride, p-nitrophenol, isocyanic acid, methyl-m-phenylene ester, 2,2'-iminodiethanol, N-(2-aminoethyl)-N'-(2-((2-aminoehtyl)amino)ethyl) 1,2-ethanediamine, 2,6-di-tert-butyl p-cresol, chloro biphenyl, 4-biphenylamine, benzyl ether, benzenesulfonyl chloride, 1,2-(methylenedioxy)-4-propenyl benzene, 2,4-diisocyanato-1-methyl benzene, chlorodinitro benzene (mixed isomers), hexahydro 2H-azepin-2-one, 4,4'-methylenedianiline, 1'-acetonaphthone, mercapto acetic acid, acetanilide, glycerol, and mixtures thereof.

6. The polysulfone semipermeable membrane of claim 4, wherein the ultra-high-molecular-weight hydrophilic polymer is polyvinylpyrrolidone.

7. The polysulfone semipermeable membrane of claim 4, wherein the polysulfone compound is selected from the group consisting of bisphenol A polysulfone, polyether polysulfone, polyphenyl polysulfone, and mixtures thereof.

8. The polysulfone semipermeable membrane of claim 4, comprising less than 3 percent by weight of ultra-high-molecular-weight hydrophilic polymer.

9. The polysulfone semipermeable membrane of claim 4, wherein the solvent is selected from the group consisting of tetramethylene sulfone, 3-methyl sulfolane, benzophenone, n,n-dimethylacetamide, 2-pyrrolidone, 3-methylsulfolene, pyridine, thiophene, o-dichlorobenzene, 1-chloronaphthalene, methyl salicylate, anisole, o-nitroanisole, diphenyl ether, diphenoxy methane, acetophenone, p-methoxyphenyl-2-ethanol, 2-piperidine, antipyrine, δ-valerolactam, diethyl phthalate, diphenyl sulfone, diphenyl sulfoxide, phthalic acid, dioctyl ester, phthalic acid, dimethyl ester, phthalic acid, diethyl ester, phthalic acid, dibutyl ester, phthalic acid, bis(2-ethylhexyl) ester, phthalic acid, benzyl butyl ester, phenyl sulfide, and mixtures thereof.

10. The polysulfone semipermeable membrane of claim 4 further comprising n-methyl-pyrrolidone.

11. The polysulfone semipermeable membrane of claim 4 wherein the non-solvent includes glycerin.

12. The polysulfone semipermeable membrane of claim 1 further comprising n-methyl-pyrrolidone.

13. The polysulfone semipermeable membrane of claim 1 comprising a non-solvent including glycerin.

14. A melt-spun polysulfone semipermeable membrane having a substantially uniform structure throughout a thickness dimension of the membrane, the polysulfone semipermeable membrane being constructed from a mixture of a melt-spun composition including greater than 35 percent by weight to about 38 percent by weight of a polysulfone compound, ultra-high-molecular-weight polyvinylpyrrolidone, a solvent for the polysulfone compound, and a non-solvent for the polysulfone compound.

15. The polysulfone semipermeable membrane of claim 14 wherein the mixture comprises n-methyl-pyrrolidone.

16. The polysulfone semipermeable membrane of claim 14, wherein the non-solvent is selected from the group consisting of 1,1-diethylurea, 1,3-diethylurea, dinitrotoluene, 1,2-ethane diamine, diphenylamine, toluenediamine, o-toluic acid, m-toluic acid, toluene-3,4-diamine, dibutyl phthalate, piperidine, decalin, cyclohexane, cyclohexene, chlorocyclohexane, cellosolve solvent, n,n-dimethylbenzylamine, paraffin, mineral oil, mineral wax, tallow amine, triethanol amine, lauryl methacrylaate, stearic acid, di(ethylene glycol), tri(ethylene glycol), ethylene glycol, poly (ethylene glycol), tetra(ethylene glycol), glycerin, diethyl adipate, d-sorbitol, chlorotriphenyl stannane, resorcinol, 2-methyl-8-quinolinol, quinaldine, 4-phenylpyridine, phosphorothioic acid, o,o-diethyl o-(p-nitrophenyl) ester, N,N-dimethyl-p-phenylene diamine, 2,6-dimethoxyphenol, 4-allyl-2-methoxyphenol, phenanthridine, 2-naphthylamine, 1-naphthylamine, 1-naphthol, 2-naphthalenethiol, 1-bromonaphthalene, levulinic acid, phenyl pyrrol-2-yl ketone, phenyl 4-pyridyl ketone, isothiocyanic acid, m-nitrophenyl ester, 2-methyl-1H-indole, 4-methyl imidazole, imadazole, 1,7-heptanediol, 9H-fluoren-9-one, ferrocene, 2,2',2"-nitrilotriethanol, 2,2'-iminodiethanol, dibenzofuran, cyclohexaneacetic acid, cyanamide, courmarin, 2,2'-bipyridine, benzoic acid, benzenepropionic acid, o-dinitrobenzene, 9-methyl-9-azabicyclo(3.3.1)nonan-3-one, chlorodiphenylarsine, antimony bromide, p-anisidine, o-anisaldehyde, adiponitrile, p-amino acetophenone, monoacetin, diacetin, triacetin, pentoxane, 4-benzoylbiphenyl, methyl oleate, triethylphosphate, butyrolactone, terphenyl, tetradecanol, polychlorinated biphenyl, myristic acid, methacrylic acid, dodecyl ester, isocyanic acid, methylenedi-p-phenylene ester, 2-((2-hexyloxy)ethoxy) ethanol, 4-nitro biphenyl, benzyl ether, benzenesulfonyl chloride, 2,4-diisocyanato-1-1-methyl benzene, adipic acid, diethyl ester, 2'-nitro-acetophenone, 1'-acetonaphthone, tetradecanone, (dichlorophenyl) trichlorosilane, dichlorodiphenyl silane, phosphorothioic acid, o,o-diethyl o-(p-nitrophenyl) ester, phosphoric acid, tri-tolyl ester, phosphoric acid, triphenyl ester, phosphoric acid, tributyl ester, phenyl phosphorous dichloride, p-nitrophenol, isocyanic acid, methyl-m-phenylene ester, 2,2'-iminodiethanol, N-(2-aminoethyl)-N'-(2-((2-aminoethyl)amino)ethyl) 1,2-ethanediamine, 2,6-di-tert-butyl p-cresol, chloro biphenyl, 4-biphenylamine, benzyl ether, benzenesulfonyl chloride, 1,2-(methylenedioxy)-4-propenyl benzene, 2,4-diisocyanato-1-methyl benzene, chlorodinitro benzene (mixed isomers), hexahydro 2H-azepin-2-one, 4,4'-methylenedianiline, 1'-acetonaphthone, mercapto acetic acid, acetanilide, glycerol, and mixtures thereof.

17. The polysulfone semipermeable membrane of claim 16 further comprising n-methyl-pyrrolidone.

18. The polysulfone semipermeable membrane of claim 14 wherein the non-solvent includes glycerin.

* * * * *